(12) United States Patent
Shimada

(10) Patent No.: US 7,475,988 B2
(45) Date of Patent: Jan. 13, 2009

(54) PERIMETER

(75) Inventor: Satoshi Shimada, Hamamatsu (JP)

(73) Assignee: Kowa Company, Ltd., Nagoya-shi (JP)

( * ) Notice: Subject to any disclaimer, the term of this patent is extended or adjusted under 35 U.S.C. 154(b) by 113 days.

(21) Appl. No.: 11/787,400

(22) Filed: Apr. 16, 2007

(65) Prior Publication Data

US 2008/0036966 A1    Feb. 14, 2008

(30) Foreign Application Priority Data

Aug. 9, 2006    (JP)    ............... 2006-217448

(51) Int. Cl.
*A61B 3/02*    (2006.01)
(52) U.S. Cl. ..................... 351/224; 351/226
(58) Field of Classification Search .......... 351/205–246
See application file for complete search history.

(56) References Cited

U.S. PATENT DOCUMENTS 5,463,431 A * 10/1995 Suzuki et al. ............... 351/226
6,685,321 B2 * 2/2004 Suzumura et al. ........... 351/224
6,783,240 B2 * 8/2004 Matsumoto ................. 351/225

FOREIGN PATENT DOCUMENTS

JP    S60 1985-241418    11/1985
JP    H08-1996-107880    4/1996

* cited by examiner

*Primary Examiner*—Mohammed Hasan
(74) *Attorney, Agent, or Firm*—Duane Morris LLP

(57) ABSTRACT

Perimeter has input means for inputting identification data of an examinee and a kind of perimetry to be conducted, means for judging whether or not the examinee has already received the perimetry, means to read examinee measurement information, means to judge whether or not a kind of inputted perimetry is different from the past perimetry, means to compute and determine initial stimulus luminance of the perimetry to be conducted from now on as a value equal to the sensitivity which is shown in sensitivity distribution data or closer thereto from the sensitivity distribution data of the past perimetry if different kind is judged, and means for starting the perimetry with the determined initial stimulus luminance.

5 Claims, 5 Drawing Sheets

(a) SCREENING PERIMETRY (b) THRESHOLD PERIMETRY (c) ISOPTER PERIMETRY (a)

(b)

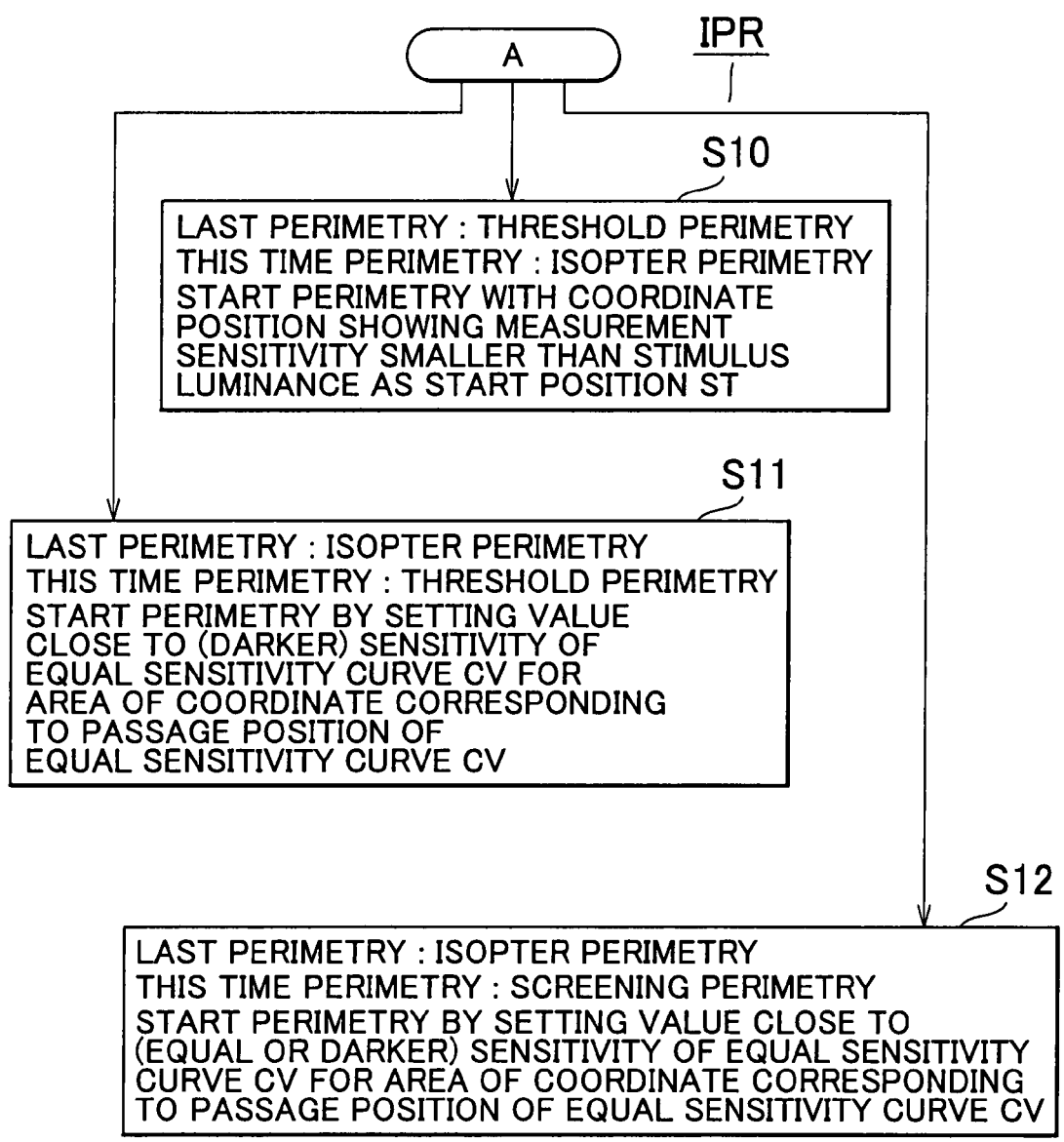

PERIMETER

BACKGROUND OF THE INVENTION

This invention relates to a perimeter for conducting two or more perimetries, such as a screening perimetry, a threshold perimetry and an isopter perimetry.

BACKGROUND ART

A longer time is necessary for a perimetry due to the fact that many points are to be measured, and a luminance level at which an examinee can see is to be judged at each measurement point. With such a situation, a Japanese patent application publication number of which is S60-241418 discloses a technique for conducting a test in a shorter time in order to lighten a burden on an examinee.

Since two or more perimetries, such as a screening perimetry, a threshold perimetry and an isopter perimetry are necessary to be selectively conducted according to a condition of an examinee when conducting a perimetry, a perimeter for conducting such a different perimetry in a shorter time while extremely lightening the burden on an examinee is desired to be developed.

Then, the object of the invention is to provide a perimeter for conducting two or more perimetries in a shorter time in order to solve the above-mentioned defects.

SUMMARY OF THE INVENTION

One aspect of the invention is perimeter for conducting two or more kinds of perimetries, comprising:
  a memory for storing a perimetry result for each examinee as sensitivity distribution data of a visual field on a visual field coordinate system as well as a kind of said perimetry conducted;
  input means for inputting identification data of an examinee and a kind of said perimetry to be conducted on said examinee;
  reexamination judging means for judging whether or not said examinee corresponding to said identification data has already received said perimetry on the basis of said identification data of said examinee which has been inputted through said input means;
  means to read examinee measurement information for searching said memory so as to read examinee measurement information which corresponds to said identification data if a judgment is that said examinee has already received said perimetry;
  perimetry kind judging means for judging whether or not said perimetry kind inputted from said input means is one different from past perimetry stored in said examinee measurement information;
  means to determine initial luminance for computing and determining an initial luminance of a stimulus in a visual field coordinate system which correspond to said perimetry to be conducted from now on so as to have a value equal to or close to a sensitivity which is shown in a sensitivity distribution data of said past perimetry on the basis of said sensitivity distribution data of said past perimetry if judgment is that said perimetry kind which has been inputted from said input means is one different from said past perimetry kind which is stored in said examinee measurement information; and
  perimetry execution means for starting said perimetry with said initial luminance which has determined by said means to determine initial luminance as said initial luminance of said stimulus.

Another aspect of the invention is the perimeter, wherein said two or more kinds of perimetries include a first perimetry of dividing a sensitivity in respective test points into two or more stages, a second perimetry of measuring said sensitivity in each test point in detail, by presenting changed luminance of said stimulus twice or more times, and a third perimetry of measuring bounds where said stimulus can be seen or bounds where said stimulus can not be seen by presenting said stimulus having some size and some luminance, moving from a predetermined movement start position.

Another aspect of the invention is the perimeter, wherein in case where a kind of said past perimetry is said third perimetry and a kind of said perimetry to be conducted from now on is said first perimetry or said second perimetry, said perimeter further has means to determine corresponding area for searching test points on said visual coordinate system in said first perimetry or said second perimetry, which correspond to passage coordinates of an equal sensitivity curve detected in said third perimetry, from sensitivity distribution data for said third perimetry, and said means to determine initial luminance computes and determines said initial luminance of said stimulus for said searched test points of said first perimetry or said second perimetry as a value equal to said sensitivity of said equal sensitivity curve or closer thereto.

Another aspect of the invention is the perimeter for conducting two or more kinds of perimetries which include a moving stimulus perimetry for measuring bounds where said stimulus can be seen or bounds where said stimulus can not be seen by presenting said stimulus having some size and some luminance, moving from a predetermined movement start position, comprising
  a memory for storing a perimetry result for each examinee as sensitivity distribution data of a visual field on a visual field coordinate system as well as a kind of said perimetry conducted;
  input means for inputting identification data of an examinee and a kind of said perimetry to be conducted on said examinee;
  reexamination judging means for judging whether or not said examinee corresponding to said identification data has already received said perimetry on the basis of said identification data of said examinee which has been inputted through said input means;
  means to read examinee measurement information for searching said memory so as to read examinee measurement information which corresponds to said identification data if a judgment is that said examinee has already received said perimetry;
  perimetry kind judging means for judging whether or not said kind of perimetry inputted from said input means is said moving stimulus perimetry and is said perimetry different from past perimetry stored in said examinee measurement information;
  means to determine stimulus movement start position, for searching said test point which shows said sensitivity corresponding to said luminance of said stimulus to be used for said moving stimulus perimetry to be conducted from now on from said sensitivity distribution data of said past perimetry, for determining said coordinate position of said searched test point on said visual field coordinate system of said moving stimulus perimetry, and for determining said movement start position of said stimulus as a position close to said determined position, when said judgment is that said kind of perimetry inputted from said input means is said moving stimulus perimetry and is said perimetry different from past perimetry stored in said examinee measurement information; and perimetry execution means for starting said moving stimulus perimetry from said movement start position determined by said means to determine stimulus movement start position.

Another aspect of the invention is the perimeter for conducting a first perimetry of dividing a sensitivity in respective test points into two or more stages, a second perimetry of measuring said sensitivity in each test point in detail, by presenting changed luminance of said stimulus twice or more times, and a third perimetry of measuring bounds where said stimulus can be seen or bounds where said stimulus can not be seen by presenting said stimulus having some size and some luminance, moving from a predetermined movement start position, comprising:

a memory for storing a perimetry result for each examinee as sensitivity distribution data of a visual field on a visual field coordinate system as well as a kind of said perimetry conducted;

input means for inputting identification data of an examinee and a kind of said perimetry to be conducted on said examinee;

reexamination judging means for judging whether or not said examinee corresponding to said identification data has already received said perimetry on the basis of said identification data of said examinee which has been inputted through said input means;

means to read examinee measurement information for searching said memory so as to read examinee measurement information which corresponds to said identification data if a judgment is that said examinee has already received said perimetry;

perimetry kind judging means for judging whether or not said perimetry kind inputted from said input means is one different from past perimetry stored in said examinee measurement information;

means to determine stimulus movement start position, for searching said test point in said first perimetry or said second perimetry which shows said sensitivity corresponding to a sensitivity of an equal sensitivity curve to be detected in said third perimetry from said sensitivity distribution data, for determining a coordinate position corresponding to said searched test point on said visual field coordinate system of said third perimetry, and for determining said movement start position of said stimulus as a position close to said determined position, when said perimetry kind judging means judges that said past perimetry kind is said first perimetry or said second perimetry, and said kind of said perimetry to be conducted from now on is said third perimetry; and perimetry execution means for starting said third perimetry from said movement start position determined by said means to determine stimulus movement start position.

According to these aspects of the invention, two or more perimetries can be conducted on an examinee who received any one of the perimetries in the past without repeating vain perimetry routines in such a manner that the perimetry is started from the initial luminance closer to the visual field sensitivity of the examinee or from the movement start position where the movement distance of the stimulus is short at the time of perimetry, thereby efficiently conducting different kinds of perimetries.

BRIEF DESCRIPTION OF THE DRAWINGS

FIGS. 4 and 5 are flowcharts showing an instance of perimetry program.

DESCRIPTION OF THE PREFERRED EMBODIMENTS

Embodiments of the invention are now explained, referring to appended drawings.

Figure 1:
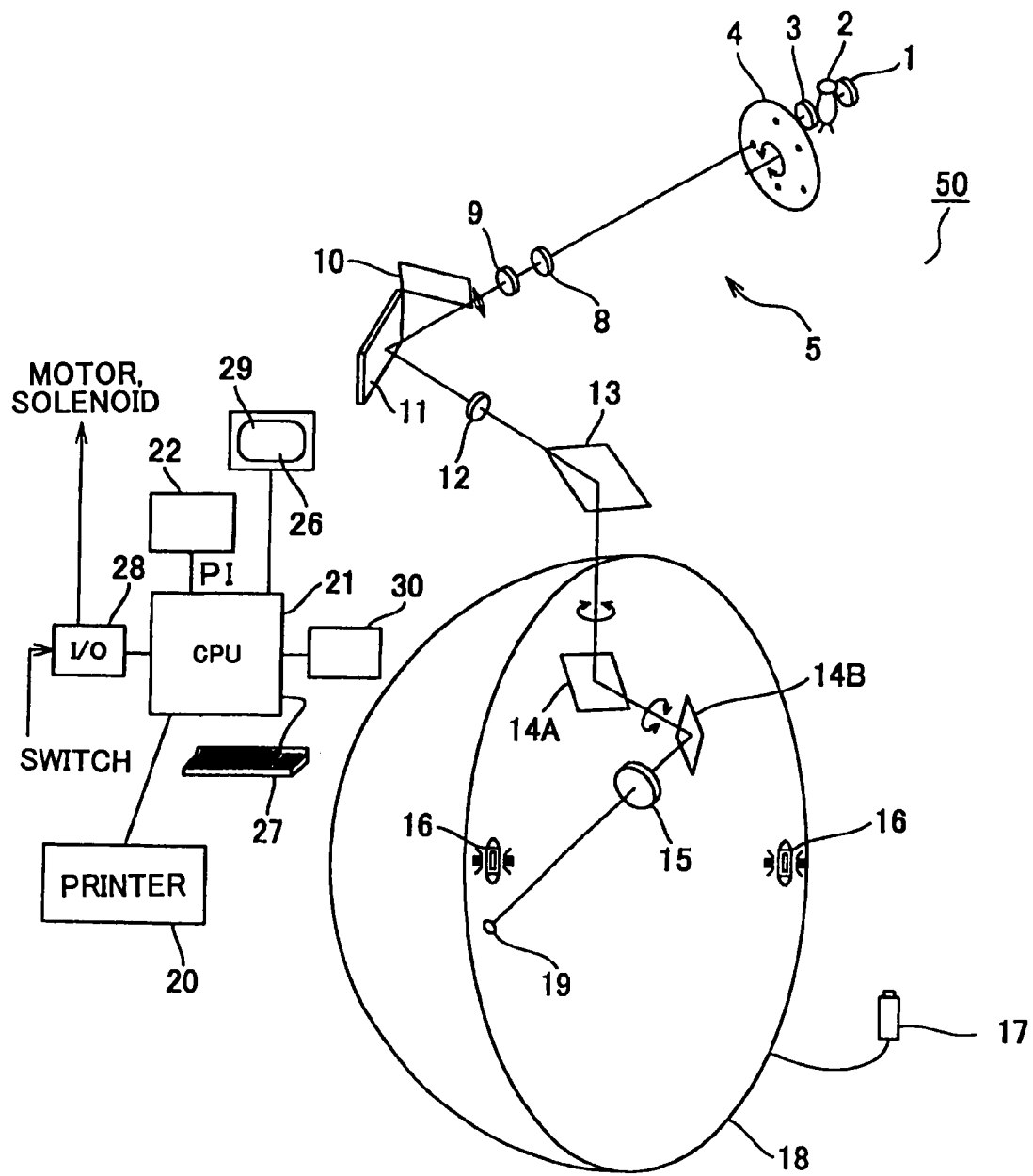
FIG. 1 is a view showing an instance of a structure of a perimeter.
Figure 2:
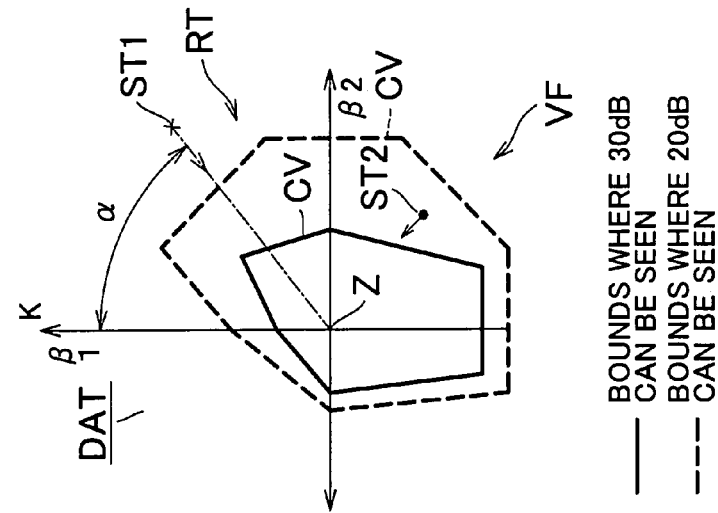
FIG. 2 is a view showing test results which are obtained by respectively different test methods in a perimetry.
Figure 2:
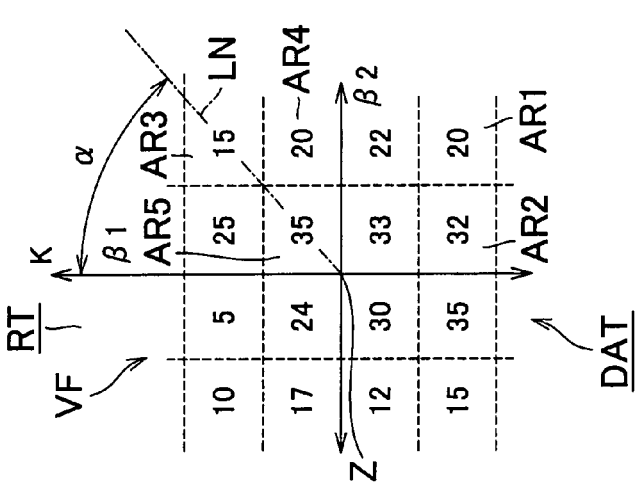
Figure 2:
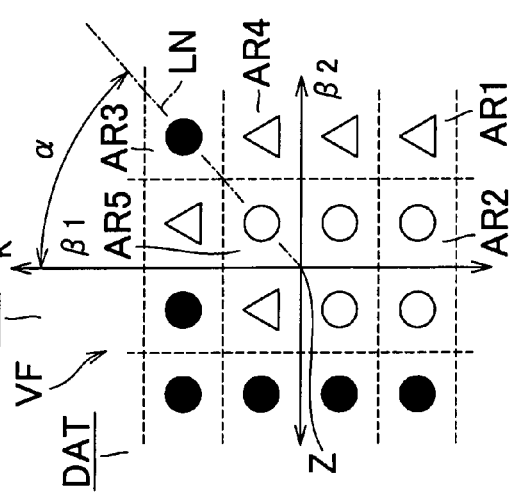
Figure 3:
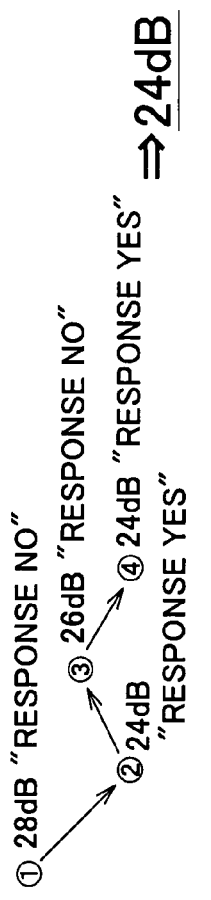
FIG. 3 is a view showing an algorithm which is used for a threshold perimetry in a perimetry.
Figure 3:
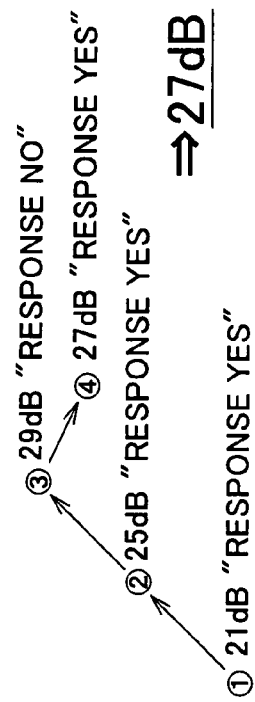
Figure 4:
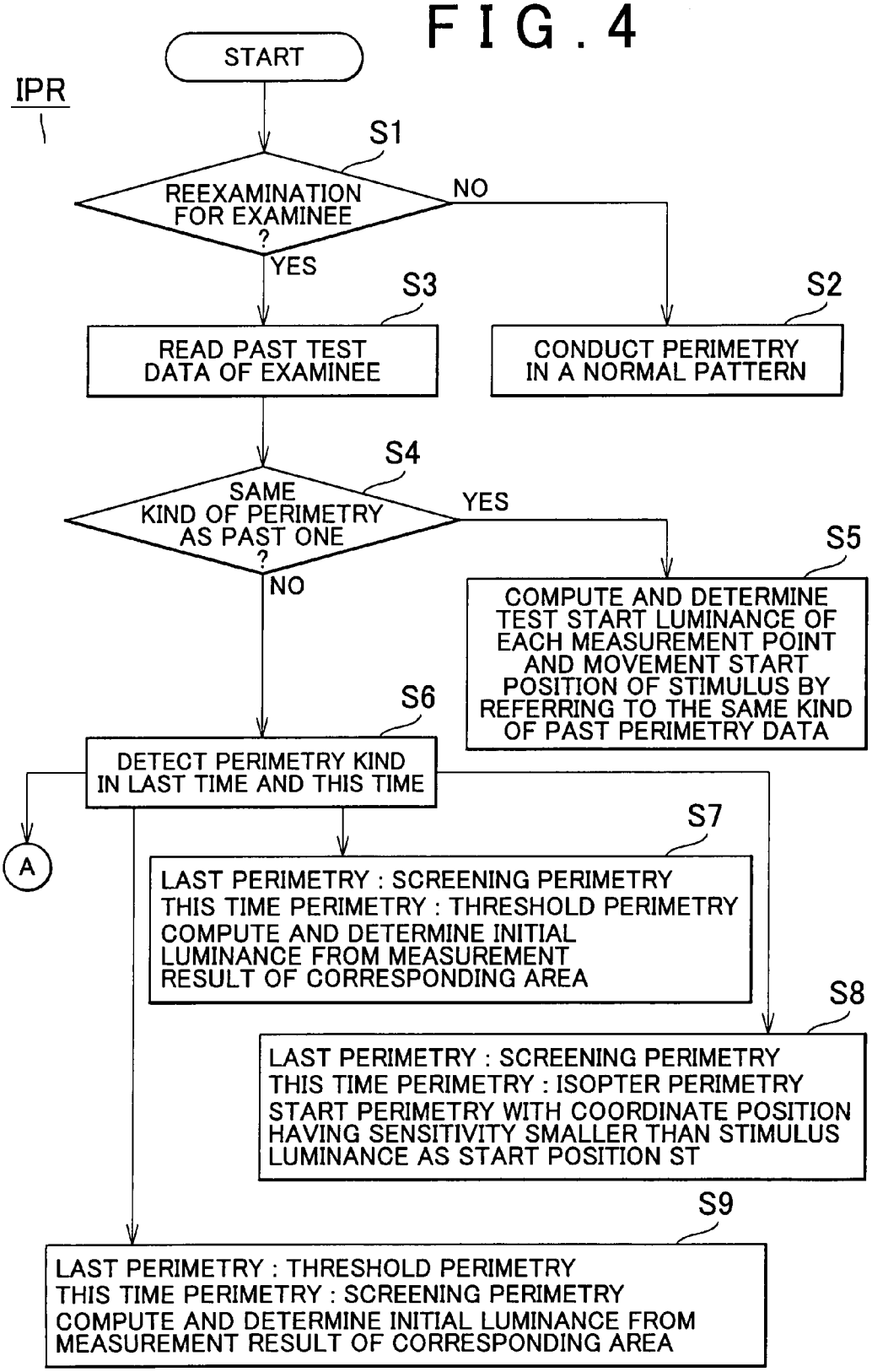

FIG. 1 is a view showing an instance of a structure of a perimeter, FIG. 2 is a view showing test results which are obtained by respectively different test methods in a perimetry, FIG. 3 is a view showing an algorithm which is used for a threshold perimetry in a perimetry, and FIGS. 4 and 5 are flowcharts showing an instance of perimetry program.

As shown in FIG. 1, a perimeter 50 has a visual field dome 18, and a chin rest (not shown) for an examinee is located at a central position of the visual field dome 18. When measuring, a position of the chin rest is aligned so as to position an eye to be examined at a center of the visual field dome 18 through an alignment mechanism (not shown). Lamps 16, 16 for background lightning are arranged inside the visual field dome 18. The perimeter having the visual field dome 18 as shown in FIG. 1 and any other perimeters can be applied to the perimeter according to the invention.

The examinee is invited to fixate a stimulus 19 which is projected on a projection plane inside the visual field dome 18, and returns a replay to an examiner by some proper method, such as by operating a response switch 17 or replying with voice when perceiving the stimulus.

In order to project the stimulus 19, a stimulus projection mechanism denoted with a reference numeral 5 is located in FIG. 1. A reference numeral 2 denotes a stimulus projection lamp (halogen lamp) as a light source, and a reflecting mirror 1 is located at the back thereof. Light of the stimulus projection lamp 2 is injected into a relay lens 8 through a condenser lens 3 and an aperture 4. The aperture 4 can determine a size of the stimulus, and has two or more openings so that a proper sized opening can be moved onto an optical axis through a control by a CPU 21 as mentioned hereinafter. Furthermore, the light is reflected by a mirror 11 after passing the relay lens 8, a focus lens 9 and (an opening of) a shutter 10, and is reflected by a mirror 13 via relay lens 12.

In this embodiment, two mirrors 14A and 14B are provided in order to control a projection position of the stimulus 19, and a swinging position of the mirror is controlled by the CPU 21 through a driving mechanism, such as a motor (not shown). Finally, the stimulus 19 is projected on the projection plane of the visual field dome 18 through a projector lens 15.

The perimeter according to the present embodiment can be used as an automatic perimeter by controlling the stimulus projecting mechanism 5 according to predetermined program with a control by the CPU 21.

A control system of the perimeter according to the present embodiment is mentioned hereinafter. The CPU 21 controls the motor which is included in the above-mentioned stimulus projecting mechanism (1 through 15) and a solenoid through an I/O port 28, and inputs information from the response switch 17.

And, a monitor 26 which is comprised of a display unit, such as a LCD and a CRT, is connected with the CPU 21, and is used for outputting test data or displaying a menu at a time of setting. A touch panel 29 (a method of detecting a coordinate is optional) is located on a screen of the monitor, and with this touch panel 29, the menu can be selected and a coordinate of a stimulus projection position can be inputted through a finger or a dedicated input pen.

An examiner can control the perimetry with the touch panel 29 or a keyboard 27. When designating one of the perimetry program and inputting a test start, the position where a stimulus is projected is controlled according to the designated perimetry program, and a response through the response switch 17 is inputted. During the perimetry, data resulting from the perimetry is stored in a memory 22 which is comprised of an optional storage device, such as a RAM and a hard disc. And, such data is displayed on the monitor 26 and is printed out with a printer 20, if necessary. The CPU 21 and memories 22, 30 function as a computer which is built in the perimeter 50.

At the time of perimetry, the stimulus which is located on the aperture 4 is projected at a proper position inside the visual field dome 18 by a well-known method. When the examinee who perceived the projected stimulus operates the response switch 17 within a predetermined limited time, the CPU 21 confirms the examinee's perception of the projected stimulus. The perimetry is conducted by a well-known method in such a way that the stimulus 19 is projected and presented to an examinee at predetermined time intervals at a lot of measurement points inside the visual field dome 18 in order to confirm in which degree the examinee perceives the stimulus.

At the time of the perimetry, the examiner selects and inputs the perimetry which is scheduled to be conducted on the examinee through the keyboard 27 or the touch panel 29. Two or more perimetry methods which can be conduced with the perimeter 50 are stored in the memory 22 (or 30) of the perimeter 50 so as to be selected as the perimetry program, and the examiner can select the proper perimetry from two or more perimetry methods which are displayed on the monitor 26, such as 1. screening perimetry, 2. threshold perimetry and 3. isopterperimetry. Other perimetry methods rather than the above-mentioned three ones can be also set so as to be selected.

The respective perimetry methods are already well-known, and various types of perimeters and the perimetry program thereof are well-known. So, detailed explanations on such each perimetry program are omitted herein, and only portions pertinent to the invention are now explained.

Perimetry data of an examinee is stored in the memory 22 (or 30) as examinee measurement information PI as well as identification information, such as ID numbers of the respective examinees. In the examinee measurement information, test points, such as an optic disc of a fundus, macula and nasal of the eye, are set and stored according to a condition, a kind or a proceeding of disease of an examinee. Besides, test methods at the time of perimetry, test patterns, past measurement results are also stored in the examinee measurement information PI in addition to the above-mentioned data. Then, these data can be read out on the basis of the ID of each examinee from a memory so as to display on the monitor 26 and can be utilized as data to be used for future perimetry.

At the time of the perimetry, the examiner inputs the identification number of the examinee through the keyboard 27. Then, the CPU 21 reads perimetry program IPR out of the memory 30, and controls contents of the perimetry according to the perimetry program IPR thereafter.

That is, in Step S1 of the perimetry program IPR as shown in FIG. 4, the CPU 21 judges whether or not the examinee measurement information PI has already been stored in the memory 22 (30), that is, whether or not the perimetry to be conducted from now on is the first one for the examinee, by referring to the examinee measurement information PI inside the memory on the basis of the inputted ID number.

If such a judgment in Step S1 is that the examinee measurement information PI of the examinee is not stored in the memory 22 (30) and the perimetry to be conducted from now on is the first one, the program enters step S2. Then, the examiner is invited to select a kind of the perimetry which will be conducted on the examinee through the keyboard 27 or the like, and various kinds of the perimetries, such as 1. screening perimetry, 2. threshold perimetry and 3. isopter perimetry, are selectively conducted with a normal test pattern.

The screening perimetry is one of dividing the sensitivities at respective test points (predetermined coordinates or areas in a visual field coordinate system VF) into two or more stages. If concerning an area AR1 of the visual field coordinate system VF, the stimulus 19 with 30 dB luminance is presented to an examinee and the examinee notices the stimulus 19 with 30 dB luminance, for instance, the sensitivity in the area AR1 is judged to be 30 dB or higher, and "white spot" is stored in the corresponding memory area. If the examinee does not notice the stimulus 19 with 30 dB luminance, the stimulus which luminance is changed into a brighter one, for instance, the 20 dB luminance is presented to the examinee at the same coordinate position (the area AR1). When the examinee can notice the stimulus 19 with 20 dB luminance, the sensitivity in the area AR1 is judged to be 20 dB through 30 dB, and "triangle" is stored in the corresponding memory area. If the examinee does not notice the stimulus 19 with 20 dB luminance, the sensitivity in the area AR1 is judged to be 20 dB or lower, and "black spot" is stored in the corresponding memory area. In such a way, the screening perimetry is one of dividing the sensitivities of the respective areas AR in the visual field coordinate system VF of the examinee into two or more stages, which respectively form a boundary of the predetermined standard luminance, such as 30 dB and 20 dB, on the basis of the information whether or not the examinee can notice the presented stimulus having the predetermined luminance.

And, the threshold perimetry is one of presenting the stimulus twice or more, changing the luminance thereof, in order to detailedly measure the sensitivity at each test point (the predetermined coordinate or the predetermined area in the visual field coordinate system VF). The luminance of the stimulus 19 is set as 21 dB, for instance, and the stimulus 19 with this luminance is positioned at a predetermined position in the visual filed area AR1 and is presented to the examinee. If the examinee perceives the stimulus 19 and presses down the response switch 17 in the above-mentioned state, the CPU 21 raises the luminance of the stimulus 19 by 4 dB (darkens the stimulus) so as to set the luminance as 25 dB, and presents the stimulus to the examinee, as shown in FIG. 3(*a*). If the examinee perceives the stimulus 19 and presses down the response switch 17 in the above-mentioned state, the CPU 21 further raises the luminance of the stimulus 19 by 4 dB (darkens the stimulus) so as to set the luminance as 29 dB, and presents the stimulus to the examinee, as shown in FIG. 3(*a*). When the examinee can not notice the stimulus 19 and does not press down the response switch 17 within the predetermined time, the CPU 21 lowers the luminance by 2 bB so as to be 27 dB (makes the stimulus brighter) by changing the luminance width from the change by 4 dB at the time of the last response by the examinee to the change by 2 dB which is narrower than the last time, and presents the stimulus which is set as 27 dB in the area AR1 in a similar way. If the examinee perceives the stimulus 19 and presses down the response switch 17 in the above-mentioned state, the retinal sensitivity in the area AR is judged to be 27 dB, and the luminance is stored in the memory corresponding to the area AR. In such a way, the sensitivity of the area AR of the examinee is determined as 27 dB.

Besides, the isopter perimetry (moving stimulus perimetry) is one of measuring the bounds wherein the examinee can see (or can not see) the stimulus having some size and some luminance. If the stimulus having 30 dB of luminance, for instance, is moved from a periphery to the center in each direction, the bounds where the examinee can see 30 dB can be obtained as equal sensitivity curve CV by connecting respective points at which the examinee responded. When the stimulus having 20 dB of luminance is moved from the center of a blind spot to the outside in each direction in order to measure the size of the blind spot, the bounds where the examinee can not see 20 dB can be obtained as the size of the blind spot by connecting respective points at which the examinee responded as equal sensitivity curve CV.

The moving direction of the stimulus is optional. But, there are mainly two stimulus moving methods, a first one of moving from a peripheral portion of the visual field coordinate system VF to an origin, and a second one of moving from a center of the area sensitivity of which is relatively low, such as the blind spot, to the outside. The moving method of the stimulus in the below-mentioned isopter perimetry is the first one.

The test method in each perimetry is well-known, and the automated measurement pattern is actually used in each perimetry.

If the judgment in step S1 is that the examinee measurement information PI of the examinee is stored in the memory 22 (30) and the perimetry to be conducted from now on is the second or later one for the examinee, the program enters step S3. Then, the past test data of the examinee is read out and is displayed on the monitor 26. As shown in FIG. 2(c), a result RT of the perimetry which has been conducted on the examinee in the past is displayed on the monitor 26, as well as test kind KD at this time, "isopter perimetry" in this case.

Subsequently, the examiner designates and inputs the kind of the perimetry to be conducted on the examinee from now on through the keyboard 27. After inputting the kind of the perimetry through the keyboard 27, the CPU 21 enters step S4 of the perimetry program IPR, and judges whether or not the perimetry which is instructed to be conducted by the examiner is the same as one which the examinee received in the past.

If the judgment in step S4 is that the perimetry which is instructed to be conducted by the examiner is the same kind of perimetry as one which the examinee received in the past, the perimetry program IPR starts the perimetry on the examinee, analyzing data corresponding to the past perimetry on the past perimetry data since the past perimetry data has been stored as the examinee measurement information PI.

In other words, when the perimetry which is instructed to be conducted by the examiner is any one of screening perimetry, threshold perimetry and isopter perimetry and the test result of the same kind of perimetry as one which is instructed to be conducted by the examiner has been already stored in the examinee measurement information PI (in the case wherein the examinee has already received the same kind of the perimetry in the past and the measurement result has already been stored), the perimetry program IPR determines a perimetry start luminance (initial luminance) in each perimetry or a moving start position of the stimulus as mentioned hereinafter.

If the perimetry which is instructed to be conducted by the examiner is the screening perimetry, the threshold perimetry or the isopter perimetry, the CPU 21 refers to the measurement result in the same kind of perimetry which the examinee has already received in the past through the perimetry program IPR. For instance, the measurement result in the screening perimetry is shown in FIG. 2(a), the measurement result in the threshold perimetry is shown in FIG. 2(b), and the measurement result in the isopter perimetry is shown in FIG. 2(c). In any perimetry, the measurement result is shown as distribution of sensitivity of visual field in the visual field coordinate system VF which is set on the visual field of the examinee (which is the radial coordinate system having an origin Z, scales of which are shown with visual field angle $\beta$ with the origin Z as its center). In the screening perimetry, the sensitivity distribution is shown with two or more areas having a predetermined sensitivity width. In the threshold perimetry, the sensitivity distribution is shown with the stimulus luminance where the sensitivity reverses, that is, with the stimulus luminance where the sensitivity is changed from perception to non-perception or from non-perception to perception. In the isopter perimetry, the sensitivity distribution is shown with the equal sensitivity curve CV having the same sensitivity.

As shown in FIG. 2(a), the measurement result of the screening perimetry is shown as the brightness of the stimulus 19 which is perceived by the examinee in a typical point (one or more points) of each area of the areas AR (test points) which are divided into two or more areas in the visual field coordinate system VF (which is set in the visual field dome 18 of FIG. 1). That is, the measurement result is shown with a map showing the retinal sensitivity of the examinee. In the map, the retinal sensitivity of each area AR is shown as a predetermined sensitivity bounds. In case of FIG. 2(a), for instance, the retinal sensitivity of the examinee which is measured in the corresponding area AR is shown with "white spot" for 30 dB or higher, with "triangle" for 20 dB through 30 dB, and with "black spot" for 20 dB or lower.

When conducting the similar screening perimetry on the examinee, the perimetry is controlled to start in such a way that the initial luminance is slightly brighter or slightly darker than the past measurement value (which is selected from the standard luminance, such as 20 dB, 30 dB and 35 dB) with reference to the measurement value of each visual field area AR of the examinee in the past screening perimetry in this perimetry since the past measurement result for the examinee in the respective visual field areas AR is already known, and a rapid progress of the retinal sensitivity is not almost desired in a general way. By doing so, it is not necessary to repeat such vain measurement operations in the perimetry to be conducted from the first that the perimetry starts with the stimulus having a dark initial (standard) luminance having no relation to the past measurement value, which can not absolutely perceived by the examinee in view of the past measurement result (In a normal measurement, the perimetry starts with the most darkest luminance irrespective of a condition of disease. For this reason, the examinee does not perceive the stimulus 19 for a while from the start of the measurement, and is burdened with vain efforts.), and for these reasons, the luminance change is forced to be repeated several times until the examinee perceives the stimulus. At the result, it is possible to finish the perimetry in a short time.

When conducting measurement on the examinee in the measurement point belonging to the area AR1, the CPU 21 judges the past measurement value to be in the bounds of 20 dB through 30 dB by referring to the measurement result at the time of the past screening perimetry according to the perimetry program IPR, as shown in FIG. 2(a). Subsequently, the CPU 21 sets the initial (standard) luminance of the stimulus 19 as 30 dB, for instance, for the area AR1, and positions the stimulus 19 with this luminance at a predetermined position in the visual field area AR1 and presents this stimulus 19 to the examinee.

If the examinee perceives the stimulus 19 in the above-mentioned state and presses down the response switch 17, the retinal sensitivity in the area AR1 is judged to be 30 dB or higher, and "white spot" is stored in the corresponding memory. On the contrary, if the examinee does not perceive the stimulus 19 and does not press down the response switch 17 within a predetermined time, the CPU 21 sets the luminance of the stimulus 19 as the next standard luminance 20 dB by lowering 10 dB so as to make brighter, and presents the stimulus in the area AR1 in a similar way. When the examinee perceives the stimulus 19 in the above-mentioned state and presses down the response switch 17, the retinal sensitivity in the area AR1 is judged to be 20 dB through 30 dB, and "triangle" is stored in the corresponding memory. Besides, if the examinee does not perceive the stimulus 19 and does not press down the response switch 17 within a predetermined time, the retinal sensitivity in the area AR1 is judged to be 20 dB or lower, and "black spot" is stored in the corresponding memory.

On the other hand, as shown in FIG. 2(b), the measurement result of the threshold perimetry is shown as the brightness of the stimulus 19 which is perceived by the examinee in a typical point (one or more points) of each area of the areas AR (test points) which are divided into two or more areas in the visual field coordinate system VF (which is set in the visual field dome 18 of FIG. 1). That is, the measurement result is shown with a map showing the retinal sensitivity of the examinee. In the map, the retinal sensitivity of each area AR is shown as a predetermined sensitivity value (the value (dB) showing the luminance of the stimulus 19 which is perceived by the examinee). In case of FIG. 2(b), for instance, the retinal sensitivity of the examinee which is measured in the corresponding area AR is read out from the memory 22 and the read sensitivity is shown.

When conducting the similar threshold perimetry on the examinee at this reexamination, the perimetry is controlled to start in such a way that the initial luminance is slightly brighter or slightly darker than the past measurement value with reference to the measurement value of each visual field area AR of the examinee in the past threshold perimetry in this perimetry since the past measurement result for the examinee in the respective visual field areas AR is already known, and a rapid progress of the retinal sensitivity is not almost desired in a general way. By doing so, it is not necessary to repeat such vain measurement operations in the threshold perimetry to be conducted from the first that the perimetry starts with the stimulus having a dark initial luminance having no relation to the past measurement value, which can not absolutely perceived by the examinee in view of the past measurement result (In a normal measurement, the perimetry starts with the luminance close to a normal sensitivity in an age of the examinee irrespective of a condition of disease. For this reason, the examinee who has widely different sensitivity from the normal sensitivity in this age does not perceive the stimulus 19 for a while from the start of the measurement, and is burdened with vain efforts.), and for these reasons, the luminance change is forced to be repeated several times until the examinee perceives the stimulus. At the result, it is possible to finish the perimetry in a short time.

When conducting measurement on the examinee in the measurement point belonging to the area AR1 according to the perimetry program IPR, the CPU 21 judges the past measurement result to be 20 dB by referring to the measurement result at the time of the past threshold perimetry which is read out from the memory 22. Subsequently, the CPU 21 sets the initial luminance of the stimulus 19 as the value close to the measurement value, 21 dB, for instance, for the area AR1, and positions the stimulus 19 with this luminance at a predetermined position in the visual field area AR1 and presents the stimulus 19 to the examinee.

If the examinee perceives the stimulus 19 in the above-mentioned state and presses down the response switch 17, the CPU 21 sets the luminance of the stimulus 19 as 25 dB by raising by 4 dB (by making darker), and presents this stimulus to the examinee. If the examinee perceives the stimulus 19 in the above-mentioned state and presses down the response switch 17 as shown in FIG. 3(a), the CPU 21 sets the luminance of the stimulus 19 as 29 B by further raising by 4 dB (by making darker), and presents this stimulus to the examinee. If the examinee does not perceive the stimulus 19 and does not press down the response switch 17 within a predetermined time, the CPU 21 changes the width of the luminance to be changed from change every 4 dB at the last response by the examinee into change every 2 dB which is narrower than the last, and sets the luminance as 27 dB by raising 2 dB (by making brighter), and presents this stimulus at the area AR1 in a similar way. If the examinee perceives the stimulus 19 in the above-mentioned state and presses down the response switch 17, the retinal sensitivity in the area AR1 is judged to be 27 dB, and this luminance is stored in the corresponding memory.

In the pattern of the luminance change in the threshold perimetry, the initial luminance is firstly made brighter, and is gradually made darker, as shown in FIG. 3(a). But, the initial luminance may be firstly made darker, and may be gradually made brighter, as shown in FIG. 3(b). Anyway, the width of the luminance change may be controlled to be smaller after the different response is received from the examinee.

As shown in FIG. 2(c), the measurement result of the isopter perimetry is shown with the equal sensitivity curve CV which is obtained by connecting positions where the examinee can perceive the stimulus 19 having a predetermined luminance which moves from a periphery of the visual field to the center for each predetermined luminance on the visual field coordinate system VF (which is set in the visual field dome 18 of FIG. 1). That is, the equal sensitivity curve CV is computed every luminance of the stimulus 19. In case of FIG. 2(c), for instance, the bounds where the examinee can perceive the stimulus 19 having luminance 30 dB is one shown with a full line in the figure, and the bounds where the examinee can perceive the stimulus 19 having luminance 20 dB is one shown with a dashed line in the figure.

When conducting the similar isopter perimetry on the examinee, the perimetry is controlled to start with the luminance of the stimulus 19 having the value equal to the past measurement value from the movement start position of the stimulus 19 which is the angular position slightly outside to the past equal sensitivity curve CV by referring to the value of the equal sensitivity curve CV at the past isopter perimetry at this time of reexamination (In case where the stimulus 19 is moved from the center, such as a blind spot, to the periphery, the stimulus 19 is controlled to start from the angular position slightly outside to the past equal sensitivity curve CV.) since the past measurement result for the examinee is already known, and a rapid progress of the retinal sensitivity is not almost desired in a general way. By doing so, it is not necessary to repeat such vain measurement operations in the isopter perimetry to be conducted from the first that the perimetry starts from the most outside peripheral portion of the normal visual field irrespective of the past measurement value (In a normal measurement, the perimetry starts from the most outside peripheral portion of the normal visual field, irrespective of a condition of disease of the examinee. For this reason, a specific examinee does not perceive the stimulus 19 for a while from the start of the measurement, and is burdened with vain efforts.), and for these reasons, the movement of the stimulus and the luminance change are forced to be repeated several times until the examinee perceives the stimulus. At the result, it is possible to finish the perimetry in a short time. If the measurement luminance of the stimulus is determined to be a constant value, such as 30 dB and 20 dB, the test result of the past isopter perimetry is used for arranging the movement start position ST at a position close to a predicted equal sensitivity curve CV at the time of the next isopter perimetry.

The CPU 21 sets the initial luminance of the stimulus 19 to be presented to the examinee as 30 dB by obtaining such an information that the past equal sensitivity curves CV are 30 dB and 20 dB and by computing passage positions of the past equal sensitivity curve CV on the visual field coordinate system VF on the basis of the perimetry program IPR with a reference to the measurement result of the past isopter perimetry. Besides, the CPU 21 sets a movement start position ST of the stimulus 19 at a position close to the outer periphery of the equal sensitivity curve CV for the luminance 30 dB by referring to the measurement result of the last isopter perimetry, not on a peripheral portion of the visual field dome 18 in FIG. 1 (In a normal measurement, the movement start position ST is set on the peripheral portion of the visual field dome 18 so as to fit for all examinees.). After setting, the perimetry is started in such a way that the stimulus is moved from this movement start position ST for the central portion at a predetermined speed.

If the CPU 21 moves the stimulus 19 from the movement start position ST for the central portion of the visual field as shown by the arrow in FIG. 2(c) and the examinee perceives the moving stimulus 19 and presses down the response switch 17, the CPU 21 computes the coordinate position of the visual field at the time when the response switch 17 is pressed down so as to display the position on the monitor 26 as well as the visual field coordinate system VF, and stores the position in the memory. Then, two or more times of perimetries are conducted by moving the stimulus from the movement start position ST which is set on the outside close to the equal sensitivity curve CV in the last measurement by the CPU 21 for the visual field center Z in different angular positions α, and the coordinate position of the visual filed is computed and is stored each time of pressing of the response switch 17 by the examinee, and the equal sensitivity curve CV is formed by connecting the response positions with each other, and this equal sensitivity curve CV is displayed on the monitor 26.

Two or more equal sensitivity curves CV as shown in FIG. 2(c) which luminance of the stimuli 19 are different are displayed by conducting two or more such actions, changing the luminance of the stimulus, and the visual field shapes can be obtained for the examinee according to the brightness, thereby.

Although the perimetry to be conducted from now on is the same kind of the perimetry as one which has been conducted in the past, perimetry conditions may be respectively different. For instance, the size or the color of the stimulus may be different in the screening perimetry or the threshold perimetry, and the size or the luminance of the stimulus is different in the isopter perimetry. In this case, difference of the conditions is also considered when computing the initial luminance or the initial position of each point in the perimetry to be conducted from the past perimetry result. If the size of the stimulus in the perimetry to be conducted is bigger than (is easier to be seen than) one which has been used in the past perimetry in the threshold perimetry, the initial luminance of each point is lowered in comparison with the past perimetry result, taking consideration of the difference of the stimulus size.

In the following case where the past perimetry method and the perimetry method to be conducted are different from each other, the difference of the perimetry condition is also considered.

If the judgment in step S4 is that the kind of the perimetry which is instructed to be conducted by the examiner is different from one of the perimetry which the examinee has received in the past, the past measurement result of the examinee is neglected and the perimetry starts with the initial luminance of the stimulus and/or from the movement start position ST, by dealing with the instructed perimetry similar to one on the examinee which has received no perimetry in the past in a conventional way. According to this conventional way, the perimetry continues with no perception of the stimulus 19 by the examinee in the first measurement of the perimetry. For this reason, a bigger burden is given to the examinee. And, vain measurement operations increase especially for the examinee whose visual field is narrow, that is, for the examinee that is necessary to receive such a perimetry, so that the measurement can not be efficiently conducted.

If the judgment in step S4 is that the perimetry which is instructed to be conducted by the examiner is a kind of perimetry different from one which the examinee has received in the past in the perimeter 50 according to the invention, the perimetry program enters step S6, and the kind of the past perimetry which is stored in the examinee measurement information PI of the examinee and the kind of the perimetry which is instructed to be conducted this time are detected.

If the past perimetry which is stored in the examinee measurement information PI of the examinee is the screening perimetry and the kind of the perimetry which is instructed to be conducted this time is the threshold perimetry as shown in step S7 of FIG. 4, a corresponding relation between the visual field area AR to be used for the screening perimetry and the visual field area AR to be used for the threshold perimetry on the visual field coordinate system VF is judged, and the area (test point) to which the coordinate position of the visual field coordinate system VF on which the threshold perimetry is conducted belongs, which corresponds to the coordinate position in each area (test point) AR on which luminance measurement has been conducted in the last screening perimetry is computed and determined. Generally, the position or the size of the area AR for the screening perimetry and of the visual field area AR for the threshold perimetry are equal, so that the area AR for the screening perimetry and the visual field area AR for the threshold perimetry are areas which correspond with each other on the visual field coordinate system VF. If the area AR for the screening perimetry and the visual field area AR for the threshold perimetry are set so as to have respectively different size and different position, but, the coordinate positions on the visual field coordinate system VF of both (concretely speaking, the measurement points on the respective areas) are compared with each other, and the area AR of the threshold perimetry which corresponds to the coordinate value for the luminance measurement in some area AR1 at the time of the screening perimetry is judged.

After thus obtaining the corresponding relation between the area to be used for the luminance measurement at the time of the screening perimetry and the area on which the threshold perimetry is conducted from now on, the CPU 21 determines the initial luminance with reference to the measurement result in the corresponding area at the time of the screening perimetry on the basis of the bounds of the luminance which is shown in the measurement result when measuring luminance in the corresponding visual filed area AR in the threshold perimetry. If the judgment is that the last measurement result in the area AR1 of the screening perimetry is "triangle" and the sensitivity of the examinee is in the bounds from 20 dB to 30 dB in FIGS. 2(a) and (b), for instance, the standard luminance at the time when the measurement result of the screening perimetry is judged to be "triangle" is 20 dB. Then, the threshold value is measured, starting from the initial luminance of the stimulus 19 in the corresponding visual field area AR1 in the threshold perimetry as 25 dB, and gradually making the luminance brighter. By doing so, the threshold value can be obtained within a shorter time in comparison with a general case of a new examinee where the measurement starts from the luminance 35 dB, for instance, which is a normal value in the point for the age of the examinee.

If the judgment is that the last measurement result in the area AR3 of the screening perimetry is "black spot" and the sensitivity of the examinee is in the bounds of 20 dB or lower in FIGS. 2(a) and (b), for instance, the threshold value is measured, starting from the initial luminance of the stimulus 19 in the corresponding visual field area AR3 in the threshold perimetry as 20 dB the same as the standard luminance with which the screening perimetry has been conducted, and gradually making the luminance brighter. By doing so, the threshold value can be obtained within a shorter time in comparison with a general case of a new examinee where the measurement starts from the luminance 35 dB, for instance, which is a normal value in the point for the age of the examinee.

If the kind of the past perimetry which is stored in the examinee measurement information PI of the examinee is the threshold perimetry and the kind of the perimetry which is instructed to be conducted this time is the screening perimetry as shown in step S9 of FIG. 4, a corresponding relation between the visual field area AR to be used for the threshold perimetry and the visual field area AR to be used for the screening perimetry on the visual field coordinate system VF is judged, and the area (test point) to which the coordinate position of the visual field coordinate system VF on which the screening perimetry is conducted belongs, which corresponds to the coordinate position in each area (test point) AR on which luminance measurement has been conducted in the last threshold perimetry is computed and determined.

After thus obtaining the corresponding relation between the area to be used for the luminance measurement at the time of the threshold perimetry and the area on which the screening perimetry is conducted from now on, the CPU 21 determines the initial luminance of the area AR in the screening perimetry with reference to the measurement result in the corresponding area at the time of the threshold perimetry on the basis of the luminance of the threshold value which is shown in the measurement result when measuring luminance in the corresponding visual filed area AR in the screening perimetry in a similar way to the above-mentioned. If the judgment is that the last measurement result in the area AR3 of the screening perimetry is "15 dB" and the threshold value of the examinee is 15 dB in FIGS. 2(a) and (b), for instance, 20 dB which is the closest to 15 dB of two or more set standard luminance and darker than 15 dB is adopted as the initial (standard) luminance of the stimulus 19 in the corresponding visual field area AR3 in the screening perimetry, and the sensitivity in the area AR3 is judged by whether or not the standard luminance of the stimulus can been seen. In this case, the sensitivity may be judged as 20 dB or lower without perceiving 20 dB of the stimulus, so that the sensitivity of the examinee can be obtained within a shorter time in comparison with a general case of a new examinee where the measurement starts from the darkest luminance 30 dB, as the above-mentioned case for instance.

If the kind of the past perimetry which is stored in the examinee measurement information PI of the examinee is the screening perimetry and the kind of the perimetry which is instructed to be conducted this time is the isopter perimetry as shown in step S8 of FIG. 4, the sensitivity of each area (test point) in the movement direction of the stimulus at the time of the isopter perimetry, that is, the sensitivity of each area (test point) on a line LN having angle α from measurement standard axis K of the visual field coordinate system VF of the screening perimetry which corresponds to the angle α from the measurement standard axis K is detected, and the area (test point) which shows the sensitivity corresponding to the stimulus luminance in the perimetry to be conducted from now on in the isopter perimetry is detected.

When measuring the sensitivity of the examinee on the line LN having angle α from the measurement standard axis K of the visual field coordinate system VF in the isopter perimetry, the CPU 21 obtains such information that the luminance in the area (test point) AR3 on the visual field coordinate system VF is 20 dB or lower which is shown by "black spot" and the luminance in the area (test point) AR5 is 30 dB or higher which is shown by "white spot" by referring the test result for the examinee on the line LN having angle α from measurement standard axis K in the past screening perimetry as shown in FIG. 2(a). Then, the CPU 21 computes and determines the coordinate position in the visual field coordinate system VF of the isopter perimetry which corresponds to the area (test point) AR3 wherein the luminance has been judged to be 20 dB or lower in the screening perimetry when measuring the sensitivity with 30 dB in the isopter perimetry to be conducted from now on.

Subsequently, the CPU 21 determines this coordinate position as the movement start position ST1 of the 30 dB of stimulus 19 in the isopter perimetry, as shown in FIG. 2(c). Thereafter, the perimetry is started by moving the stimulus 19 for the visual field center Z. Then, the sensitivity of the examinee at the start position ST1 of the isopter perimetry has already been known as 20 dB or lower in the last screening perimetry, and the 30 dB of the equal sensitivity curve CV may be on the visual field center Z side rather than this position with higher possibility. When starting the isopter perimetry with the initial luminance 30 dB from the start position ST1, therefore, it is possible to start the perimetry from the inside position of the visual field coordinate system VF rather than the peripheral portion of the visual field dome 18 by starting the perimetry with the initial luminance 30 dB from the start position ST1, thereby making the movement distance of the stimulus at the time of the perimetry shorter. As the result, the rapid perimetry is possible.

If the kind of the past perimetry which is stored in the examinee measurement information PI of the examinee is the threshold perimetry and the kind of the perimetry which is instructed to be conducted this time is the isopter perimetry as shown in step S10 of FIG. 5, the sensitivity of each area (test point) in the movement direction of the stimulus at the time of the isopter perimetry, that is, the sensitivity of each area (test point) on a line LN having angle α from measurement standard axis K of the visual field coordinate system VF of the threshold perimetry which corresponds to the angle α from the measurement standard axis K is detected, and the area (test point) which shows the sensitivity corresponding to the stimulus luminance in the perimetry to be conducted from now on in the isopter perimetry is detected.

When measuring the sensitivity of the examinee on the line LN having angle a from the measurement standard axis K of the visual field coordinate system VF in the isopter perimetry, the CPU 21 obtains such information that the luminance in the area (test point) AR3 on the visual field coordinate system VF is 15 dB and the luminance in the area (test point) AR5 is 35 dB as shown in FIG. 2(b) by referring the test result for the examinee on the line LN having angle a from measurement standard axis K in the past threshold perimetry. Then, the CPU 21 computes and determines the coordinate position in the visual field coordinate system VF of the isopter perimetry which corresponds to the area (test point) AR3 wherein the luminance has been judged to be 15 dB in the threshold perimetry when measuring the sensitivity with 30 dB in the isopter perimetry to be conducted from now on.

Subsequently, the CPU 21 determines this coordinate position as the movement start position ST1 of the 30 dB of stimulus 19 in the isopter perimetry, as shown in FIG. 2(c). Thereafter, the perimetry is started by moving the stimulus 19 for the visual field center Z. Then, the sensitivity of the examinee at the start position ST1 of the isopter perimetry has already been known as 15 dB in the last threshold perimetry, and the 30 dB of the equal sensitivity curve CV may be on the visual field center Z side rather than this position with higher possibility. Therefore, it is possible to start the perimetry from the inside position of the visual field coordinate system VF rather than the peripheral portion of the visual field dome 18 by starting the isopter perimetry with the initial luminance 30 dB from the start position ST1, and the rapid perimetry is possible, thereby.

If the kind of the past perimetry which is stored in the examinee measurement information PI of the examinee is the isopter perimetry and the kind of the perimetry which is instructed to be conducted this time is the threshold perimetry as shown in step S11 of FIG. 5, the CPU 21 firstly extracts the coordinates passing on the equal sensitivity curve CV in the visual field coordinate system VF at the time of the isopter perimetry which are shown in sensitivity distribution data DAT. Subsequently, the CPU 21 computes the corresponding relation of the extracted passage coordinates with the visual field coordinate system VF in the threshold perimetry, and computes and judges the visual field area AR (test point) in the threshold perimetry which passes the equal sensitivity curve CV having a predetermined sensitivity which has been measured in the last isopter perimetry on the visual field coordinate system VF of the threshold perimetry.

That is, the CPU 21 obtains the area where the equal sensitivity curve CV passes on the visual field area AR in the threshold perimetry as shown in FIGS. 2(b) and (c) in the last isopter perimetry. For instance, the CPU 21 obtains the visual field area in the threshold perimetry (the areas AR1 and AR4, for instance) which the 20 dB of the equal sensitivity curve CV passes. The luminance in this area and the area close thereto is predicted to be 20 dB or so, also in the threshold perimetry. Then, the threshold perimetry is started with the initial luminance of the stimulus 19 as the value equal to 20 dB which is the sensitivity of the equal sensitivity curve CV shown in the sensitivity distribution data DAT or closer (the darker one), with 25 dB or so, for instance, at the time of the threshold perimetry on the area. By doing so, the perimetry can be conducted within a shorter time in comparison with such a general measurement case where the measurement starts from the initial luminance 35 dB, for instance, which is a normal value in the point for the age of the examinee.

If the kind of the past perimetry which is stored in the examinee measurement information PI of the examinee is the isopter perimetry and the kind of the perimetry which is instructed to be conducted this time is the screening perimetry as shown in step S12 of FIG. 5, the CPU 21 firstly extracts the coordinates passing on the equal sensitivity curve CV in the visual field coordinate system VF at the time of the isopter perimetry which are shown in the sensitivity distribution data DAT. Subsequently, the CPU 21 computes the corresponding relation of the extracted passage coordinates with the visual field coordinate system VF in the screening perimetry, and computes the visual field area AR (test point) in the screening perimetry which passes the equal sensitivity curve CV having a predetermined sensitivity which has been measured in the last isopter perimetry on the visual field coordinate system VF of the screening perimetry.

That is, the CPU 21 obtains the area corresponding to the coordinates which pass the equal sensitivity curve CV on the visual field area AR in the screening perimetry as shown in FIGS. 2(a) and (c) in the last isopter perimetry. For instance, the CPU 21 obtains the visual field area in the screening perimetry (the areas AR4 and AR3, for instance) which the 20 dB of equal sensitivity curve CV passes. The luminance in this area and the area close thereto is predicted to be 20 dB or so, also in the screening perimetry. Then, the threshold perimetry is started with the standard luminance (initial luminance) (any one of 20 dB and 30 dB) of the stimulus 19 as 20 dB which is the sensitivity of the equal sensitivity curve CV shown in the sensitivity distribution data DAT at the time of the threshold perimetry on the area. By doing so, the perimetry can be conducted within a shorter time in comparison with such a general measurement case where the measurement starts from the initial luminance 30 dB which is the darkest standard luminance in this instance.

The above-mentioned initial luminance value can be optionally set, and optional setting is possible depending on examinees or an object for measurement. In the invention, any setting on the luminance and the test start position is optional as long as the position corresponding to each test position of the visual field coordinate system VF which shows the test result of the different kind of the past perimetry is obtained on the visual field coordinate system VF for the perimetry to be newly conducted, and the luminance of the stimulus or the test start position at this position is set as the luminance close to the test result in the different kind of the perimetry or the coordinate position close to the obtained one so as to start the perimetry.

The invention can be utilized as a perimeter for conducting two or more different perimetries.

The present invention has been explained on the basis of the example embodiment discussed. Although some variations have been mentioned, the embodiments which are described in the specification are illustrative and not limiting. The scope of the invention is designated by the accompanying claims and is not restricted by the descriptions of the specific embodiments. Accordingly, all the transformations and changes within the scope of the claims are to be construed as included in the scope of the present invention.

The invention claimed is:

1. Perimeter for conducting two or more kinds of perimetries, comprising:

a memory for storing a perimetry result for each examinee as sensitivity distribution data of a visual field on a visual field coordinate system as well as a kind of said perimetry conducted;

input means for inputting identification data of an examinee and a kind of said perimetry to be conducted on said examinee;

reexamination judging means for judging whether or not said examinee corresponding to said identification data has already received said perimetry on the basis of said identification data of said examinee which has been inputted through said input means;

means to read examinee measurement information for searching said memory so as to read examinee measurement information which corresponds to said identification data if a judgment is that said examinee has already received said perimetry;

perimetry kind judging means for judging whether or not said perimetry kind inputted from said input means is one different from past perimetry stored in said examinee measurement information;

means to determine initial luminance for computing and determining an initial luminance of a stimulus in a visual field coordinate system which correspond to said perimetry to be conducted from now on so as to have a value equal to or close to a sensitivity which is shown in a sensitivity distribution data of said past perimetry on the basis of said sensitivity distribution data of said past perimetry if judgment is that said perimetry kind which has been inputted from said input means is one different from said past perimetry kind which is stored in said examinee measurement information; and perimetry execution means for starting said perimetry with said initial luminance which has determined by said means to determine initial luminance as said initial luminance of said stimulus.

2. The perimeter according to claim 1, wherein said two or more kinds of perimetries include a first perimetry of dividing a sensitivity in respective test points into two or more stages, a second perimetry of measuring said sensitivity in each test point in detail, by presenting changed luminance of said stimulus twice or more times, and a third perimetry of measuring bounds where said stimulus can be seen or bounds where said stimulus can not be seen by presenting said stimulus having some size and some luminance, moving from a predetermined movement start position.

3. The perimeter according to claim 2, wherein in case where a kind of said past perimetry is said third perimetry and a kind of said perimetry to be conducted from now on is said first perimetry or said second perimetry, said perimeter further has means to determine corresponding area for searching test points on said visual coordinate system in said first perimetry or said second perimetry, which correspond to passage coordinates of an equal sensitivity curve detected in said third perimetry, from sensitivity distribution data for said third perimetry, and said means to determine initial luminance computes and determines said initial luminance of said stimulus for said searched test points of said first perimetry or said second perimetry as a value equal to said sensitivity of said equal sensitivity curve or closer thereto.

4. Perimeter for conducting two or more kinds of perimetries which include a moving stimulus perimetry for measuring bounds where said stimulus can be seen or bounds where said stimulus can not be seen by presenting said stimulus having some size and some luminance, moving from a predetermined movement start position, comprising a memory for storing a perimetry result for each examinee as sensitivity distribution data of a visual field on a visual field coordinate system as well as a kind of said perimetry conducted;

input means for inputting identification data of an examinee and a kind of said perimetry to be conducted on said examinee;

reexamination judging means for judging whether or not said examinee corresponding to said identification data has already received said perimetry on the basis of said identification data of said examinee which has been inputted through said input means;

means to read examinee measurement information for searching said memory so as to read examinee measurement information which corresponds to said identification data if a judgment is that said examinee has already received said perimetry;

perimetry kind judging means for judging whether or not said kind of perimetry inputted from said input means is said moving stimulus perimetry and is said perimetry different from past perimetry stored in said examinee measurement information;

means to determine stimulus movement start position, for searching said test point which shows said sensitivity corresponding to said luminance of said stimulus to be used for said moving stimulus perimetry to be conducted from now on from said sensitivity distribution data of said past perimetry, for determining said coordinate position of said searched test point on said visual field coordinate system of said moving stimulus perimetry, and for determining said movement start position of said stimulus as a position close to said determined position, when said judgment is that said kind of perimetry inputted from said input means is said moving stimulus perimetry and is said perimetry different from past perimetry stored in said examinee measurement information; and perimetry execution means for starting said moving stimulus perimetry from said movement start position determined by said means to determine stimulus movement start position.

5. Perimeter for conducting a first perimetry of dividing a sensitivity in respective test points into two or more stages, a second perimetry of measuring said sensitivity in each test point in detail, by presenting changed luminance of said stimulus twice or more times, and a third perimetry of measuring bounds where said stimulus can be seen or bounds where said stimulus can not be seen by presenting said stimulus having some size and some luminance, moving from a predetermined movement start position, comprising:

a memory for storing a perimetry result for each examinee as sensitivity distribution data of a visual field on a visual field coordinate system as well as a kind of said perimetry conducted;

input means for inputting identification data of an examinee and a kind of said perimetry to be conducted on said examinee;

reexamination judging means for judging whether or not said examinee corresponding to said identification data has already received said perimetry on the basis of said identification data of said examinee which has been inputted through said input means;

means to read examinee measurement information for searching said memory so as to read examinee measurement information which corresponds to said identification data if a judgment is that said examinee has already received said perimetry;

perimetry kind judging means for judging whether or not said perimetry kind inputted from said input means is one different from past perimetry stored in said examinee measurement information;

means to determine stimulus movement start position, for searching said test point in said first perimetry or said second perimetry which shows said sensitivity corresponding to a sensitivity of an equal sensitivity curve to be detected in said third perimetry from said sensitivity distribution data, for determining a coordinate position corresponding to said searched test point on said visual field coordinate system of said third perimetry, and for determining said movement start position of said stimulus as a position close to said determined position, when said perimetry kind judging means judges that said past perimetry kind is said first perimetry or said second perimetry, and said kind of said perimetry to be conducted from now on is said third perimetry; and perimetry execution means for starting said third perimetry from said movement start position determined by said means to determine stimulus movement start position.

* * * * *